United States Patent [19]

Kantor

[11] Patent Number: 4,564,677
[45] Date of Patent: Jan. 14, 1986

[54] PREPARATION OF N-AMINO COMPOUNDS

[75] Inventor: Martin L. Kantor, Mamaroneck, N.Y.

[73] Assignee: USV Pharmaceutical Corp., Tarrytown, N.Y.

[21] Appl. No.: 571,977

[22] Filed: Jan. 19, 1984

[51] Int. Cl.[4] .................. C07B 31/00; C07B 43/02
[52] U.S. Cl. .................................. 544/164; 544/59; 544/382; 546/244; 548/483; 548/557; 564/314; 564/465; 260/239 B
[58] Field of Search .................. 544/164, 382, 59; 548/483, 557; 564/465; 260/239 B; 546/244

[56] References Cited

U.S. PATENT DOCUMENTS 2,802,031  8/1957  Horvitz .................. 564/465

Primary Examiner—Robert W. Ramsuer

[57] ABSTRACT

Disclosed is a method of preparing N-amino compounds from corresponding secondary amines by reacting a secondary amine with nitrous acid and zinc in a neutral pH reaction media to form the corresponding N-amine.

2 Claims, No Drawings

PREPARATION OF N-AMINO COMPOUNDS

This invention relates to the preparation of N-amino compounds which are useful as intermediates in the preparation of starting materials and intermediates for synthesizing chemical compounds useful in the chemical industry, such as dyes and pigments, and as pharmaceutically active compounds.

The N-amino compounds are synthesized from the corresponding secondary amines by first treating a secondary amine:

with nitrous acid or its equivalent in a suitable water-miscible solvent, followed by treatment with zinc under neutral pH conditions and then isolating the N-amino compound having the moiety

by crystallization, distallation, or reaction with a strong acid.

The synthesis according to the present invention is simple, economical, safe and is an advantageous alternative to making N-amino compounds from N-nitroso amines, which are known carcinogens.

The present invention encompasses the synthesis of N-amino compounds with the following structures from the corresponding secondary amines:

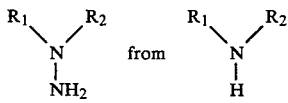   I.

wherein:

$R_1$ and $R_2$ are independently lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms;

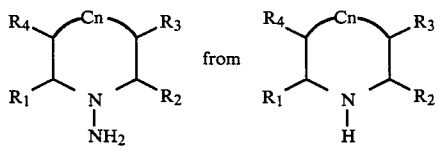   II.

wherein:

n is 0–3;

$R_1$ and $R_2$ are independently H, lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms;

$R_3$ and $R_4$ are independently H, lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms; and when taken together with the carbon atoms to which they are attached and the carbon atom denoted by Cn, $R_3$ and $R_4$ form a cycloalkyl group containing 4 to 7 carbons; a benzo group; or benzo group substituted with halogen, hydroxy, carboxy, trifluoromethyl, lower alkyl having 1 to 4 carbon atoms, or lower alkoxy having 1 to 4 carbon atoms;

$R_1$ and $R_4$, when taken together with the carbon atoms to which they are attached form a cycloalkyl group containing 4 to 7 carbons; a benzo group; or a benzo group substituted with halogen, hydroxy, carboxy, trifluoromethyl, lower alkyl having 1 to 4 carbon atoms, or lower alkoxy having 1 to 4 carbon atoms;

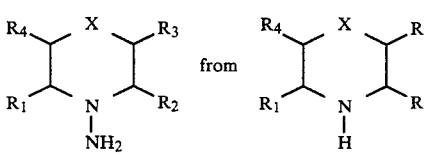   III.

wherein:

$R_1$ and $R_2$ are independently H; lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms;

$R_3$ and $R_4$ are independently H; lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms, and when taken together with the carbon atoms to which they are attached and with the X atom, $R_3$ and $R_4$ form a cycloalkyl group containing 4 to 7 atoms;

$R_1$ and $R_4$ when taken together with the carbon atoms to which they are attached form a cycloalkyl group containing 4 to 7 carbons; a benzo group; or a benzo group substituted with halogen, hydroxy, carboxy, trifluoromethyl, lower alkyl having 1 to 4 carbon atoms, or lower alkoxy having 1 to 4 carbon atoms; and X is O; S; N; or N substituted with lower alkyl containing 1 to 6 carbon atoms; cycloalkyl containing 3 to 7 carbon atoms; phenyl; phenyl substituted with halogen, hydroxy, carboxy, trifluoromethyl, lower alkyl having 1 to 4 carbon atoms, or alkoxy having 1 to 4 carbon atoms;

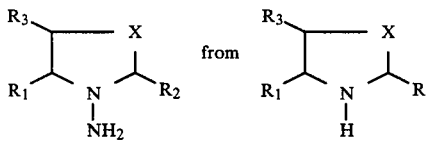   IV.

wherein:

$R_1$, $R_2$, and $R_3$ are independently H; lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms;

$R_2$ and $R_3$ when taken together with the carbon atoms to which they are attached and with the X atom form a cycloalkyl group containing 4 to 7 carbon atoms;

$R_1$ and $R_3$ when taken together with the carbon atoms to which they are attached form a cycloalkyl group containing 4 to 7 carbons; a benzo group; or benzo group substituted with halogen, hydroxy, carboxy, trifluoromethyl, lower alkyl having 1 to 4 carbon atoms, or lower alkoxy having 1 to 4 carbon atoms; and X is O; S; N; or N substituted with lower alkyl containing 1 to 6 carbon atoms, cycloalkyl containing 3 to 7 carbon atoms; phenyl; phenyl substituted with halogen, hydroxy, carboxy, trifluoromethyl, lower alkyl having 1 to 4 carbon atoms, or lower alkoxy having 1 to 4 carbon atoms.

The method of preparing the N-amino compounds comprises the steps of:

dissolving a secondary amine in a suitable solvent, such as methanol, ethanol, isopropanol or acetonitrile;

reacting the dissolved compound with nitrous acid or its equivalent to form an N-nitroso derivative;

reacting the N-nitroso derivative in situ with zinc under neutral pH conditions to form the N-amino compound;

separating the N-amino compound by crystallization, distillation or reaction with a strong acid.

More particularly, the synthesis of the N-amino compounds is carried out by first dissolving the secondary amine starting material in a water-miscible solvent of which methanol is preferred. The solution so-obtained is then cooled to a temperature of about 0° to 30° C., preferably to about 5 to 15° C. Next, the pH of the cooled solution is adjusted to 3 or below, preferably to about 1. When adjusting the pH, large excess of acid should be avoided. A nitrite salt is then added to the solution at a rate such that the temperature of the solution remains at or below 30° C. and preferably at about 5° to 15° C. For the purpose of convenience, the nitrite salt may be added in the form of a water solution. The pH of the resulting mixture is raised to about 6 to 9, preferably to about 7 to 7.5. Zinc dust is then added with sufficient agitation to keep the same suspended in the solution followed by slow addition of an ammonium salt of a weak acid. It is preferred to add the ammonium salt in the form of a water solution to provide for later partitioning of the aqueous and organic phases during the workup of the reaction mixture. After completion of the reaction the mixture may be filtered to remove unreacted zinc. The reaction product is then separated by extraction into toluene or other suitable solvents followed by removal of the solvent and isolation of the product by crystallization, distillation, salt formation, or other suitable prior art recognized methods.

The starting materials used in the process of the present invention are secondary amines that are readily available from commercial sources and/or may be prepared using standard synthetic methods and starting materials. For example, the following starting materials are available from the indicated sources:

2-methylindoline from Dastech and Orlex; alkylamines from Virginia Chemical, Pennwalt and BASF; morpholine from Ashland Chemical, BASF and Texaco; pyrrolidine from BASF and American Hoechst; dicyclohexylamine from Abbott, Monsanto and American Hoechst; hexamethyleneimine from BASF; and piperidine from Abbott, Reilly Tar and Howard Hall.

The following examples will illustrate the method of the present invention.

EXAMPLE 1

1-Amino-2-Methylindoline 140 g of 2-methylindoline was dissolved in 1 liter of methanol. About 95 ml of concentrated hydrochloric acid was added and the solution was cooled to 15° C. Then a 25% solution of sodium nitrite (73 g) in water was added dropwise at 5°–10° C. The pH of the solution was adjusted to about 7.5 with sodium bicarbonate and 156 g of zinc dust was added to form a mixture thereof. Keeping the mixture at about 5° C., a solution of 264 g of ammonium carbonate in 1 liter of water was added over a period of about 1.5 hours. The mixture was then stirred at 5°–10° C., warmed to 40° C., and filtered. The residual was washed with toluene. The combined filtrate and washes were separated and the aqueous layer was discarded. The toluene was removed in vacuo and the residue recrystallized from heptane to give 1-amino-2-methylindoline. TLC test confirmed the identity of the product compound. (ANALTECH Silica Gel plate; chloroform/acetic acid:9/1).

EXAMPLE 2

1-Amino-2-Methylindoline Methanesulfonate 10 g of crude 1-amino-2-methylindoline (made as described in Example 1) was dissolved in 40 ml of isopropanol. 6.75 g of methanesulfonic acid was added and the solution was cooled to about 0° C. to obtain crystals of 1-amino-2-methylindoline methanesulfonate which was isolated by filtration. The crystals were then washed by slurrying with fresh isopropanol and dried at 20° C. Melting range of product compound was 170°–2° C.

EXAMPLE 3

1-Amino-2-Methylindoline Hydrochloride 135.9 g of 2-methylindoline was dissolved in 750 ml of methanol and 100 ml of concentrated hydrochloric acid was added. The solution was cooled to 15° C. and a 33% solution of sodium nitrite in water was added slowly until the presence of excess nitrite was observed. This reaction mixture was stirred for 30 minutes followed by the addition of 100 g of ammonium acetate. The reaction mixture was cooled to 25°–30° C. and 160 g of zinc dust was added over a period of 20 minutes. Then 670 g of ammonium acetate was added in small portions over a period of 40 minutes. The mixture was stirred for about 60 minutes and then extracted four times with a total of 1 liter of toluene. To the combined toluene extract was added 100 ml of concentrated hydrochloric acid and 80 g of ice. The mixture was cooled and filtered to obtain a solid product. The solid product was washed with toluene and then with acetone and dried. The dried product melted at 272°–4° C. and showed one spot at Rf 0.58 on the Analtech Silica Gel plate, mobile phase hexane/ethylacetate/acetic acid - 7/3/1.

EXAMPLE 4

1-Amino-2-Methylindoline Hydrochloride 140 g of 2-methylindoline was dissolved in 750 ml of acetonitrile. 110 ml of concentrated hydrochloric acid was added and the solution was cooled. A solution of 75 g of sodium nitrite in 300 ml of water was added dropwise. The pH of the solution was adjusted to about 7 with ammonium acetate followed by portionwise addition of 160 g of zinc dust and 385 g of ammonium acetate. Next, 100 ml of water was added and the mixture was stirred for about 2 hours at 45° C. The solids were filtered off and washed with toluene (3×250 ml). The tolune washes were then used to extract the filtrate. The toluen washes were then combined, acidified with 120 ml of concentrated hydrochloric acid and 120 g of ice was added to obtain the crystals of the title compound. The crystals were separated by filtration, washed with toluene and dried. The dried material was checked by TLC and was of good quality.

EXAMPLE 5

N-Aminomorpholine 90 g of morpholine was dissolved in 1 liter of methanol. 95 ml of concentrated hydrochloric acid was added and the solution was cooled to 15° C. A 25% solution of sodium nitrite in water was added dropwise until starch-iodide paper showed a positive reaction. The pH was adjusted to about 7.5 with ammonium acetate and then 156 g of zinc dust was added. The mixture was kept at about 5° C. and a solution of 423 g of ammonium acetate in water was added over a period of about 1.5 hours. The mixture was then filtered and the filtrate was extracted with toluene. The toluene was removed by distillation and the title product, N-aminomorpholine, was distilled at 168° C. at 760 mm.

EXAMPLE 6

N-Aminopyrrolidine Hydrochloride 71 g of pyrrolidine was dissolved in 500 ml of methanol followed by the addition of concentrated hydrochloric acid until the pH of about 1 was reached. The solution was then cooled to about 10° C. and a solution of 70 g sodium nitrite in 200 ml of water was slowly added. After stirring for about 15 minutes, 20 g of ammonium acetate was added. Next, 160 g of zinc dust was added, followed by the portionwise addition of 700 g of ammonium acetate. After stirring for about 60 minutes, the mixture was extracted with 500 ml of toluene. The toluene extract was dried and hydrogen chloride gas was passed in until no further precipitation occurred. The resulting crystals, after purification, melted at 108°-110° C.

The process of preparing other members of the N-amino compounds is analogous to the process illustrated by the above examples. It is to be noted, however, that when a large amount of water is present in proportion to the amount of the solvent in which the secondary amine is dissolved (methanol), the reaction does not proceed to an acceptable degree as shown by Example 7 which follows.

EXAMPLE 7

In a beaker with stirring, 10.6 ml of concentrated hydrochloric acid was charged, followed by the addition of 80 ml of water. 16 g of 2-methylindoline was added and the mixture was stirred to dissolve the compound. The pH was then adjusted to 2-3 and the solution was cooled to 5° C. A 25% solution of sodium nitrite in water was added slowly until starch-iodide paper showed the presence of excess nitrite. The pH was then adjusted to 7 by the addition of sodium bicarbonate, followed by the addition of 75 ml of methanol. Next, 13 g of zinc dust was added, followed by the addition over 1.25 hours of a solution of 29 g of ammonium carbonate in 120 ml of water. The mixture was then warmed to 50° C. and the inorganic solids were removed by filtration. The solids were washed with toluene, which in turn was used to extract the aqueous filtrate. Examination of the toluene extract, using TLC, showed 2-methylindoline, N-nitroso-2-methylindoline, and only traces of N-amino-2-methylindoline.

While the above examples describe the preparation of certain compounds which are illustrative of the novel synthetic process, it is to be understood that the invention is not be be limited to the preparation of the specific compounds or by the specific reaction conditions described, but is to be understood to embrace variations and modifications thereof.

What is claimed is:

1. A method of preparing an N-amino compound of the formula

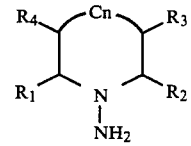

from a secondary amine of the formula

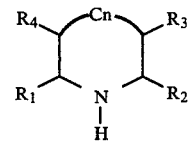

wherein:
n is 0–3;
$R_1$ and $R_2$ are independently H; lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms;
$R_3$ and $R_4$ are independently H; lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms, and when taken together with the carbon atoms to which they are attached and the carbon atom denoted by Cn, $R_3$ and $R_4$ form a cycloalkyl group containing 4 to 7 carbon atoms; a benzo group; or benzo group substituted with halogen, hydroxy, carboxy, trifluoromethyl, lower alkyl having 1 to 4 carbon atoms, or lower alkoxy having 1 to 4 carbon atoms;
$R_1$ and $R_4$, when taken together with the carbon atoms to which they are attached form a cycloalkyl group containing 4 to 7 carbon atoms; a benzo group; or a benzo group substituted with halogen, trifluoromethyl, hydroxy, carboxy, lower alkyl having 1 to 4 carbon atoms, or lower alkoxy having 1 to 4 carbon atoms; said method comprising the steps of:
dissolving the secondary amine in a water-miscible solvent;

reacting said secondary amine with nitrous acid, followed by reaction with zinc in a neutral pH reaction media containing an ammonium salt to form the corresponding N-amine; and separating said N-amine from the reaction media.

2. A method of preparing an N-amino compound of the formula

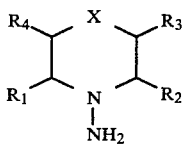

from a secondary amine of the formula

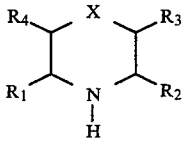

wherein:

R$_1$ and R$_2$ are independently H, lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms;

R$_3$ and R$_4$ are independently H, lower alkyl containing 1 to 6 carbon atoms; cycloalkyl containing 3 to 7 carbon atoms; phenyl; phenyl substituted with halogen, trifluoromethyl, hydroxy, carboxy, lower alkyl having 1 to 4 carbon atoms, lower alkoxy having 1 to 4 carbon atoms, or lower alkenyl containing 1 to 6 carbon atoms, and when taken together with the carbon atoms to which they are attached and with the X atom, form a cycloalkyl group containing 4 to 7 atoms;

R$_1$ and R$_4$, when taken together with the carbon atoms to which they are attached form a cycloalkyl group containing 4 to 7 carbons; a benzo group; or a benzo group substituted with halogen, trifluoromethyl, hydroxy, carboxy, lower alkyl having 1 to 4 carbon atoms or lower alkoxy having 1 to 4 carbon atoms; and X is O; S or N substituted with lower alkyl containing 1 to 6 carbon atoms, cycloalkyl containing 3 to 7 carbon atoms; phenyl; phenyl substituted with halogen, hydroxy, carboxy, trifluoromethyl, lower alkyl having 1 to 4 carbon atoms, or lower alkoxy having 1 to 4 carbon atoms; said method comprising the steps of:

dissolving the secondary amine in a water-miscible solvent;

reacting said secondary amine with nitrous acid, followed by reaction with zinc in a neutral pH reaction media containing an ammonium salt to form the corresponding N-amine; and separating said N-amine from the reaction media.

* * * * *